(12) United States Patent
Metzbower (10) Patent No.: US 7,320,596 B2
(45) Date of Patent: Jan. 22, 2008

(54) CARTRIDGE FOR VISCUOS DENTAL MATERIAL

(75) Inventor: Curt E. Metzbower, Wyoming, DE (US)

(73) Assignee: Dentsply International Inc., York, PA (US)

( * ) Notice: Subject to any disclaimer, the term of this patent is extended or adjusted under 35 U.S.C. 154(b) by 223 days.

(21) Appl. No.: 10/727,861

(22) Filed: Dec. 4, 2003

(65) Prior Publication Data
US 2004/0152041 A1 Aug. 5, 2004

Related U.S. Application Data

(60) Provisional application No. 60/431,961, filed on Dec. 9, 2002.

(51) Int. Cl.
*A61C 5/04* (2006.01)

(52) U.S. Cl. ..................................... 433/90

(58) Field of Classification Search ............ 433/89, 433/90, 80; 222/631, 572, 575, 386
See application file for complete search history.

(56) References Cited

U.S. PATENT DOCUMENTS

| | | | |
|---|---|---|---|
| 2,836,333 A | 5/1958 | Woodel | 222/575 |
| 4,330,280 A | 5/1982 | Dougherty et al. | 433/90 |
| 4,391,590 A * | 7/1983 | Dougherty | 433/90 |
| 4,617,918 A * | 10/1986 | Donohue et al. | 601/162 |
| 4,619,613 A * | 10/1986 | Dragan | 433/90 |
| 4,768,954 A | 9/1988 | Dragan | 433/90 |
| 5,033,650 A * | 7/1991 | Colin et al. | 222/137 |
| 5,122,057 A | 6/1992 | Discko, Jr. | 433/90 |
| 5,165,890 A | 11/1992 | Discko, Jr. | 433/90 |
| 5,172,807 A | 12/1992 | Dragan et al. | 206/219 |
| 5,267,859 A * | 12/1993 | Discko, Jr. | 433/89 |
| 5,322,440 A | 6/1994 | Steele | 433/90 |
| 5,379,927 A | 1/1995 | Montenieri et al. | 222/546 |
| 5,401,254 A * | 3/1995 | Bunce | 604/218 |
| 5,460,523 A * | 10/1995 | Schulman | 433/90 |
| 5,707,234 A * | 1/1998 | Bender | 433/90 |
| 5,816,453 A * | 10/1998 | Spencer et al. | 222/321.3 |
| 5,848,894 A | 12/1998 | Rogers | 433/90 |
| 6,099,307 A | 8/2000 | Discko, Jr. | 433/90 |

(Continued)

FOREIGN PATENT DOCUMENTS

DE  3428030  9/1985

(Continued)

*Primary Examiner*—Ralph A. Lewis
(74) *Attorney, Agent, or Firm*—Daniel W. Sullivan; James B. Bieber; Douglas J. Hura (57) ABSTRACT

The invention provides a method of extruding dental material from a capsule-like cartridge, by providing a capsule-like cartridge having an elongated body and a nozzle. The elongated body has an inner chamber wall enclosing dental material. The nozzle has an inner channel wall, and a channel wall exit orifice rim. The inner chamber wall has a chamber wall exit port rim, opening between the inner chamber wall and the inner channel wall. The chamber wall exit port rim has a chamber wall exit port rim effective diameter $D_1$. The inner channel wall has an inner channel wall effective diameter $D_2$. The inner channel wall effective diameter $D_2$ effectively is greater than the chamber wall exit port rim effective diameter $D_1$.

22 Claims, 7 Drawing Sheets

U.S. PATENT DOCUMENTS

| | | | |
|---|---|---|---|
| 6,261,094 B1 | 7/2001 | Dragan | 433/90 |
| 6,379,152 B1 | 4/2002 | Dragan | 433/90 |
| 6,422,866 B2 | 7/2002 | Dragan et al. | 433/90 |
| 6,503,084 B2 * | 1/2003 | Evers et al. | 433/226 |
| 2004/0063063 A1 * | 4/2004 | Cheetham et al. | 433/90 |
| 2005/0147939 A1 * | 7/2005 | Zumkeller | 433/90 |

FOREIGN PATENT DOCUMENTS

| | | |
|---|---|---|
| EP | 0919206 | 6/1999 |
| EP | 1010400 | 6/2000 |
| EP | 1147747 | 10/2001 |
| EP | 0696993 | 6/2002 |
| FR | 2501080 A * | 9/1982 |
| GB | 2251385 | 7/1992 |
| GB | 2259901 | 3/1993 |
| WO | 98/00071 | 1/1998 |

* cited by examiner

CARTRIDGE FOR VISCUOS DENTAL MATERIAL

This application claims the benefit of U.S. Provisional patent application No. 60/431,961 filed Dec. 9, 2002.

The invention relates to cartridges having an inner chamber and a passage from a chamber into a nozzle. The invention provides improved cartridges having a passage from a chamber a widened nozzle. The nozzle is wider than the passage from the chamber.

DETAILED DESCRIPTION OF THE PREFERRED EMBODIMENT

Figure 1:
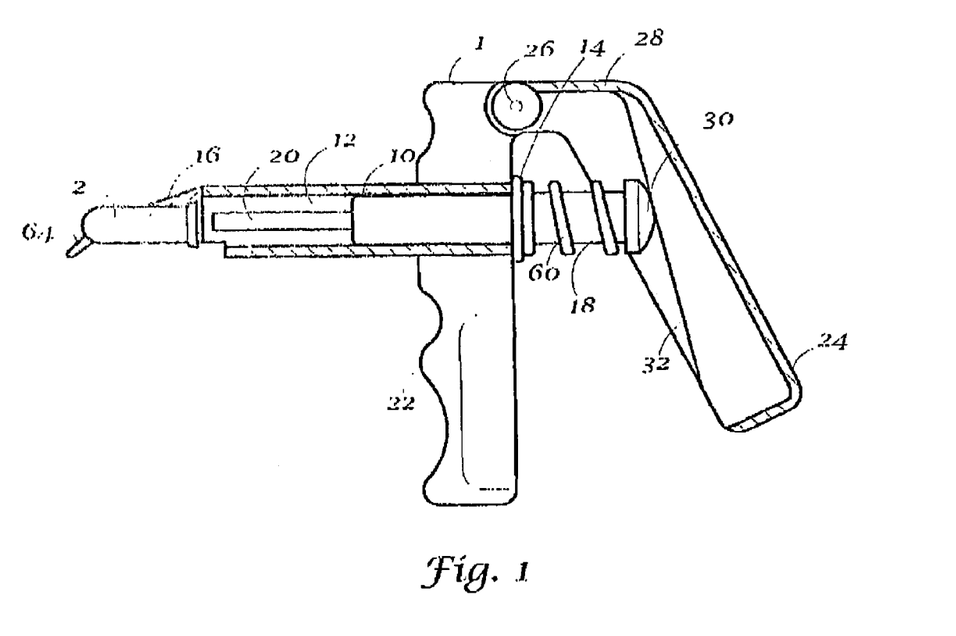
FIG. 1 is a side elevation of an ejector holder for supporting a capsule-like cartridge in accordance with the invention.
Figure 2:
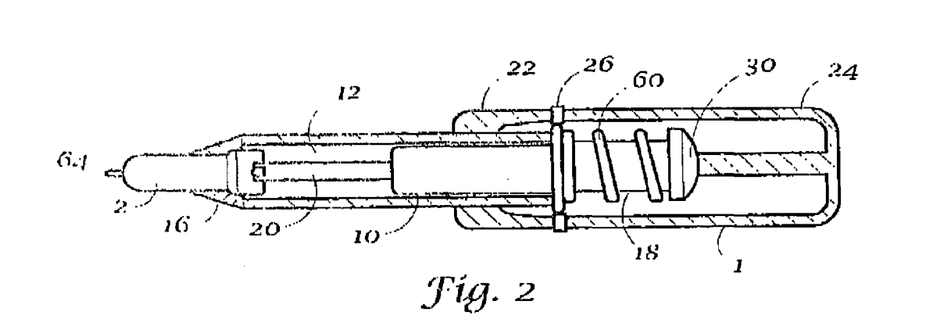
FIG. 2 is a top plan view of the holder and cartridge shown in FIG. 1.
Figure 3:
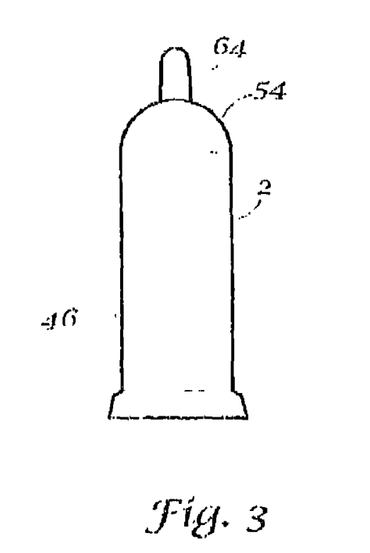
FIG. 3 is a top view of a cartridge in accordance with the invention.

The invention is now described with more particular reference to FIGS. 1 though 14. With more particular reference to FIGS. 1 and 2, is seen capsule-like cartridge 2 in accordance with the invention being held in operative position in ejector holder 1. Holder 1 has a barrel 10 with an interior bore 12 extending from the rearward end 14 of the barrel toward the forward end 16 thereof for receiving a plunger 18 of the same diameter as that of the interior bore 12 for the major portion of the length of the plunger, the forward end of the plunger has a smaller diameter extension 20. The rearward end 14 of the barrel 10 extends through and is fixed to a handle member 22 with which the barrel 10 is perpendicular. Pivotally connected to the handle 22 is an operating lever 24, the upper end of which is pivotally connected to the upper end of handle 22 by a pivot pin 26. The upper end 28 of operating lever 24 is offset laterally to facilitate operation of the lever 24 with respect to the outer end of plunger 18 which terminates in a button 30 engageable by the inner surface 32 of operating lever 24.

With more particular reference to FIGS. 3 through 6, is seen capsule-like cartridge 2. Cartridge 2 includes elongated body 46, nozzle 64, and piston 68. Elongated body 46 is molded from rigid plastic material and has a cylindrical body wall 48. Cylindrical body wall 48 has an inner chamber wall 50, which is generally cylindrical, and has a predetermined length, a uniform interior diameter, a uniform exterior diameter and a central axis. One end of the cylindrical body wall is open and formed at the extremity thereof with an annular relatively short circular exterior flange 52. Flange 52 is adapted to be detachably mounted within a complementary seat in an ejector type holder. The opposite end of the body is closed by an end wall 54 having a hemispherical exterior surface 56 and an arcing interior surface 58. End wall 54 has substantially greater thickness than cylindrical body wall 48. Preferably, the thickness of the thickest cross-section of end wall 54 is at least 20 percent greater than the average cross-sectional thickness of cylindrical body wall 48. More preferably, the thickness of the thickest cross-section of end wall 54 is at least 30 percent greater than the average cross-sectional thickness of cylindrical body wall 48. Preferably, the thickest cross-section of end wall 54 is on the opposite side of the central axis of cylindrical body wall 48 from nozzle 64. Preferably, end wall 54 is generally semi-circular in cross-section on the opposite side of the central axis of cylindrical body wall 48 from nozzle 64.

Figure 4:
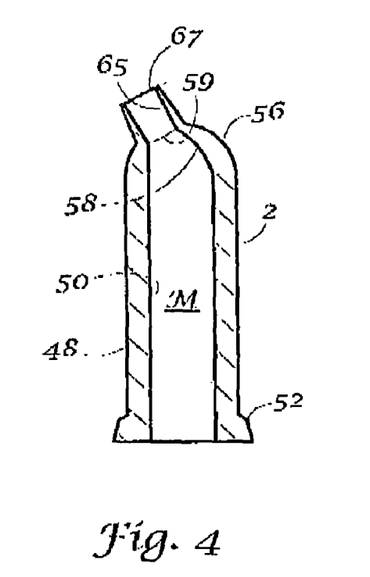
FIG. 4 is a cross-sectional side view of the cartridge shown in FIGS. 3 through 6.
Figure 4A:
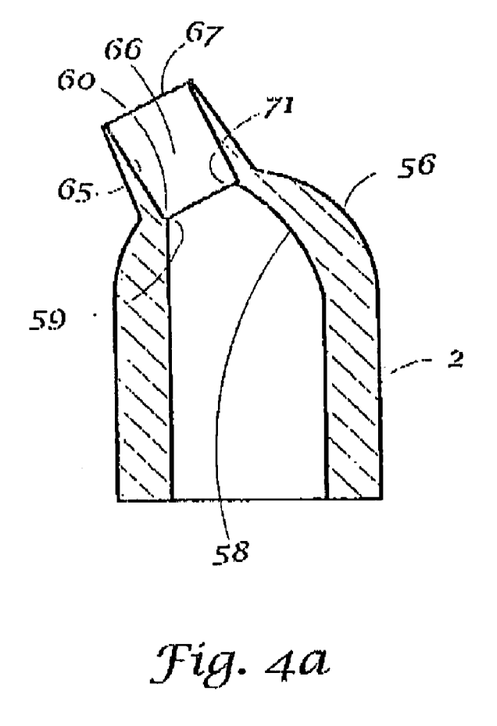
FIG. 4A is a partial cross-sectional side view of the cartridge shown in FIGS. 3 through 6.
Figure 4B:
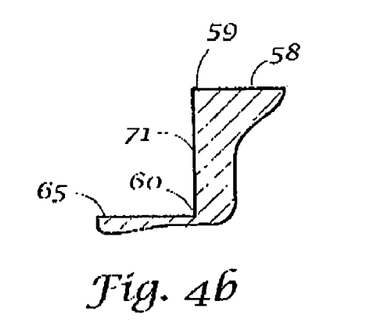
FIG. 4B is a partial cross-sectional side view along line L of the nozzle entrance passage of the cartridge shown in FIGS. 3 through 6.

Nozzle 64 is molded integrally with and extends from end wall 54 at an obtuse angle to the central axis of cylindrical body wall 48. Nozzle 64 is adapted to direct the discharge of viscous dental material M from cartridge 2 to a tooth in the interior of the oral cavity of a patient. Nozzle 64 has an inner channel wall 65 enclosing nozzle channel 66. Inner channel wall 65 is effectively uniformly cylindrical. Inner channel wall 65 has channel wall exit orifice rim 67. Nozzle 64 has nozzle entrance passage 71, through the end wall 54 to inner channel wall 65. Inner channel wall 65 has an effectively uniform diameter. Nozzle entrance passage 71 extends from chamber wall exit port rim 59 to nozzle entrance passage rim 60. Chamber wall exit port rim 59 has a chamber wall exit port rim diameter $D_1$. Nozzle entrance passage rim 60 has a nozzle entrance passage rim diameter $D_2$. Nozzle entrance passage rim 60, and inner channel wall 65 effectively have the same diameter: $D_2$ Nozzle entrance passage rim diameter $D_2$ is substantially greater than chamber wall exit port rim diameter $D_1$.

Piston 68 has cylindrical outer side wall 72, which is closely complementary to inner chamber wall 50 and inserted into the open end of cartridge 2 to form a combination closure and ejector. Viscous dental material M enclosed by cylindrical inner cartridge body wall 50 is forced by piston 68 into the opening of chamber wall exit port rim 59 through nozzle entrance passage 71, through the opening of entrance passage rim 60 then into nozzle channel 66 enclosed by inner channel wall 65 and then out channel wall exit orifice rim 67. Preferably, channel wall exit orifice rim 67 is positioned adjacent to a natural dental tooth while viscous dental material M is being forced therefrom.

In use dental material M is extruded from the nozzle of capsule-like cartridge 2. The nozzle has an inner channel wall 65, and a channel wall exit orifice rim 67. Inner chamber wall 50 opens through chamber wall exit port rim 59, into nozzle channel 66, which is enclosed by inner channel wall 65. Chamber wall exit port rim 59 has a chamber wall exit port rim effective diameter $D_1$. Inner channel wall 65 has an inner channel wall effective diameter $D_2$. Inner channel wall effective diameter $D_2$ is effectively substantially greater than the chamber wall exit port rim effective diameter $D_1$.

Preferably, the cylindrical chamber wall has a cylindrical chamber wall effective diameter $D_3$. Preferably, the cylindrical chamber wall effective diameter $D_3$ is greater than the inner channel wall effective diameter $D_2$.

Preferably, the diameter of chamber wall exit port rim 59 of nozzle entrance passage 71 is at least 3 percent less than, the diameter of inner channel wall 65 (and the diameter of entrance passage rim 60 of nozzle entrance passage 71). More preferably, the diameter of chamber wall exit port rim 59 of nozzle entrance passage 71 is at least 5 percent less than, the diameter of inner channel wall 65 (and the diameter of entrance passage rim 60 of nozzle entrance passage 71). Most preferably, the diameter of chamber wall exit port rim 59 of nozzle entrance passage 71 is at least 10 percent less than, the diameter of inner channel wall 65 (and the diameter of entrance passage rim 60 of nozzle entrance passage 71). Preferably, the length of entrance passage 71 is less than 20 percent of the diameter of chamber wall exit port rim 59.

Preferably, the length of entrance passage 71 is more than 1 percent of the diameter of chamber wall exit port rim 59. More preferably, the length of entrance passage 71 is more than 3 percent of the diameter of chamber wall exit port rim 59. The length $EP_L$ of entrance passage 71 is about one half the change in diameter of the passageway while going from elongated body 46 to nozzle 64. For nozzle entrance passage in accordance with the invention, it is preferred that the length of entrance passage is from about one half to about equal to the change in diameter of the passageway while going from elongated body to nozzle.

Figure 4C:
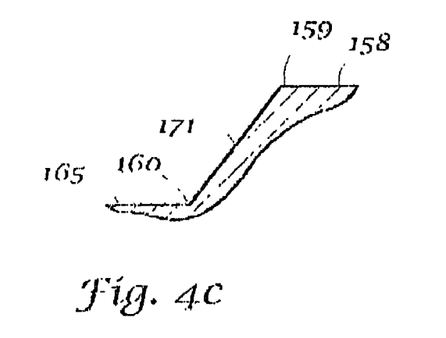
FIGS. 4C and 4D are partial cross-sectional side views along lines corresponding to line L, and showing alternative slopes for the nozzle entrance passage of the cartridge shown in FIGS. 3 through 6.
Figure 4D:
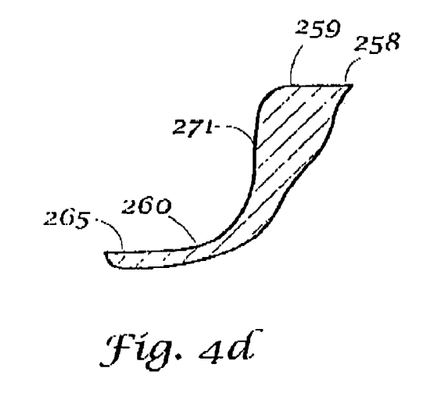
Figure 5:
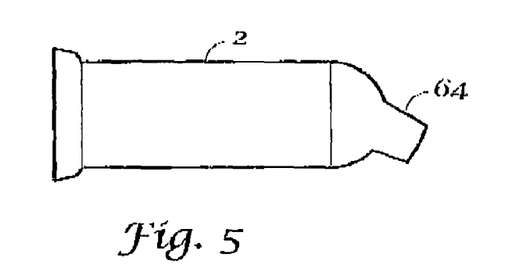
FIG. 5 is a side view of the cartridge shown in FIGS. 3 through 6.
Figure 6:
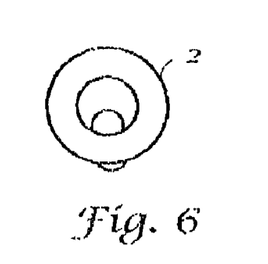
FIG. 6 is a rear view of the cartridge shown in FIGS. 3 through 6.

With more particular reference to FIGS. 4C and 4D are seen alternative slopes for the nozzle entrance passage of the cartridge shown in FIGS. 3 through 6. A partial cross-section of nozzle entrance passage 171 is planar, as shown in FIG. 4C. A line in the surface of nozzle entrance passage 171 intersects a line in the surface of arcing interior surface 158 at entrance port 159 at an acute angle. A line in the surface of nozzle entrance passage 171 intersects a line in the surface of cylindrical inner nozzle wall 165 at exit port 160 at an acute angle. A partial cross-section of nozzle entrance passage 271 is planar in the middle and curved at its ends, as shown in FIG. 4D. A line in the planar portion of nozzle entrance passage 271 intersects a line in the surface of arcing interior surface 258 at entrance port 259 at an acute angle. A line in the planar portion of nozzle entrance passage 271 intersects a line in the surface of cylindrical inner nozzle wall 265 at exit port 260 at an acute angle.

Figure 7:
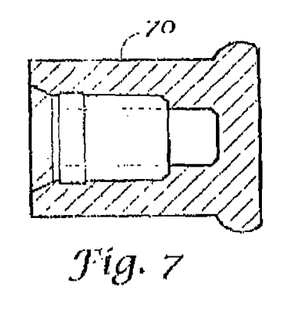
FIG. 7 is a cross-sectional side view of a cap for use in the cartridge shown in FIGS. 1 through 6.
Figure 8:
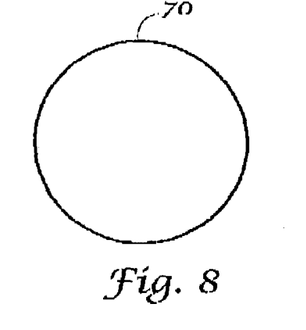
FIG. 8 is an end view of the cap shown in FIG. 7.

With more particular reference to FIGS. 7 and 8 is seen cap 70. Cap 70 is cup-shaped to frictionally engage nozzle 64. Cap 70 and/or nozzle 64 may have threads formed therein or thereon to secure cap 70 on nozzle 64. Cap 70 seals the contents of cartridge 2, and may be color-coded for example, to indicate the weight, color, quantity, and/or setting time of material contained in cartridge 2.

Figure 9:
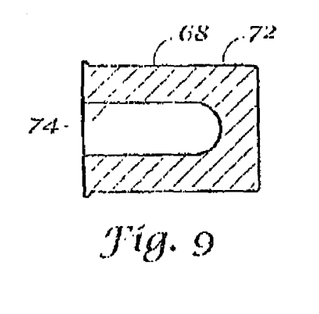
FIG. 9 is a cross-sectional side view of a plug for use in the cartridge shown in FIGS. 1 through 6.
Figure 10:
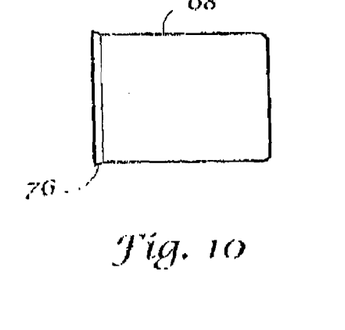
FIG. 10 is a side view of the plug shown in FIG. 9.
Figure 11:
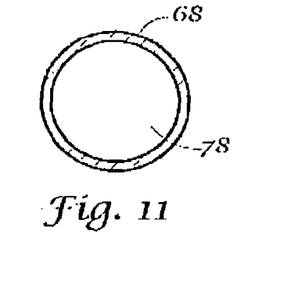
FIG. 11 is an end view of the plug shown in FIG. 9.

With more particular reference to FIGS. 9 through 11 is seen piston 68. Piston 68 has cylindrical outer side wall 72, an inner chamber piston wall 74, flange 76 and a circular front face 78. Cylindrical outer side wall 72 is closely complementary to cylindrical inner cartridge body wall 50. Piston 60 is inserted into the open end of cartridge 2 (adjacent to flange 52) to form a closed cartridge 2.

Figure 12:
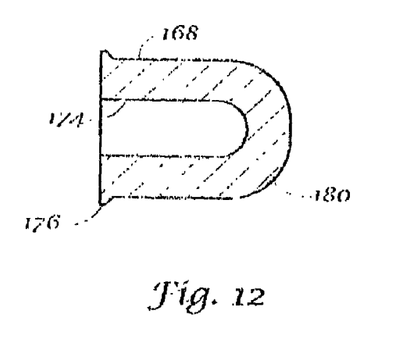
FIG. 12 is a cross-sectional side view of a plug for use in the cartridge shown in FIGS. 1 through 6.
Figure 13:
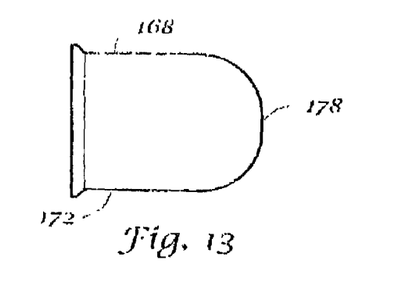
FIG. 13 is a side view of the plug shown in FIG. 12.
Figure 14:
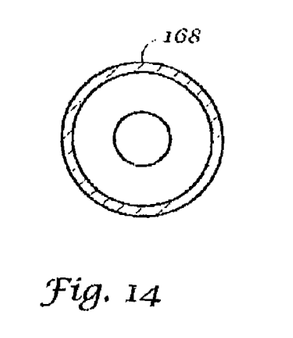
FIG. 14 is an end view of the plug shown in FIG. 12.

With more particular reference to FIGS. 12 through 14 is seen piston 168. Piston 168 is useful in place of piston 68 in cartridge 2. Piston 168 has a cylindrical outer wall 172, an inner chamber wall 174, flange 176 and a circular front face 178 on a hemispherical front end 180.

Cartridge 2 is preferably formed by molding rigid synthetic resin or plastic material. Cartridge 2 is filled with a dental material, such as dental filling material, cement. Cartridge 2 includes a piston 68, which is very closely complementary in diameter to the interior of the cartridge 2, and the inner end 69 thereof also is hemispherical and complementary to the interior of the closed end 62 of the cartridge.

Also, the body of cartridge 2, cap 70 and piston 68 may all be molded from similar plastic material. They are preferably opaque to the transmission of ambient light, when light curable dental material is enclosed in cartridge 2.

A compule cartridge in accordance with a preferred embodiment of the invention has a 0.080 inch diameter exit port wall from the body into a nozzle with a 0.100 inch diameter nozzle inner wall has an extrusion force decrease of 20-30 percent compared to the same cartridge except with a 0.100 inch diameter exit port wall from the body into a nozzle. i.e. having no constriction in the feed passage into the 0.100 inch diameter nozzle.

Figure 15:
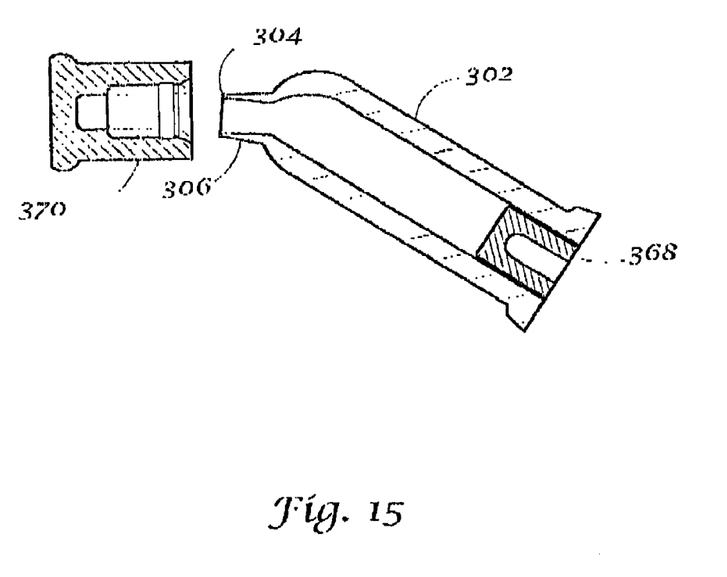
FIG. 15 is a cross-sectional side view of a cartridge having a bead around its nozzle and with a piston inserted in accordance with the invention.

With more particular reference to FIG. 15 is seen cartridge 302 having bead 304 around nozzle 306. Bead 304 functions as a flange, rim or collar. Piston 368 is inserted into cartridge 302. Except for bead 304, cartridge 302 is the same as cartridge 2. Bead 304 circumscribes nozzle 306 and retains cap 370 on nozzle 306. Preferably bead 304 is positioned in the central region of the outer surface of nozzle 306. Preferably bead 304 is positioned within 30 percent of the midpoint of the length of the outer surface of nozzle 306.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

What is claimed is:

1. A method of extruding dental material from a cartridge, comprising:

providing a cartridge having an elongated body, a nozzle, and a piston, said elongated body having an inner chamber wall and end wall portion, said elongated body enclosing dental material, and, said nozzle having a cylindrical nozzle channel with a substantially uniform diameter, an inner channel wall enclosing said nozzle channel, and a channel wall exit orifice rim, said nozzle extending from said end wall portion of said elongated body, said inner chamber wall having a chamber wall exit port rim, said chamber wall exit port rim having an opening and being connected to said inner chamber wall of said elongated body and said inner channel wall of said nozzle, said chamber wall exit port rim having a chamber wall exit port rim effective diameter $D_1$, said nozzle channel having an effective diameter $D_2$, said nozzle channel effective diameter $D_2$ effectively being greater than said chamber wall exit port rim effective diameter $D_1$, said end wall portion of said elongated body having a hemispherical exterior surface and an arcing interior surface, said end wall portion having substantially greater thickness than said inner chamber wall of said elongated body, and said piston being inserted into said elongated body, wherein said piston has a side wall and semi-circular front-facing portion, said side wall being complementary to said inner chamber wall of said elongated body and said front-facing portion having a complementary shape to said interior surface of said end wall portion of said elongated body, and applying force to said piston to extrude said dental material through said nozzle of said cartridge.

2. The method of claim 1 wherein said cartridge further comprises a cap, said cap being supported by said nozzle.

3. The method of claim 2 wherein said nozzle extends from said body and said cap closes an outer end of said nozzle to seal the contents of the cartridge against ingress of any surrounding contaminating matter.

4. The method of claim 2 wherein said cap is color-coded to indicate desired properties of the contents of the cartridge.

5. The method of claim 1 wherein said piston and said body are formed from plastic material, said plastic material being impervious to the transmission of ambient light, thereby rendering the cartridge adapted to contain light-curable material in a manner to prevent premature curing of such material while stored in such cartridge.

6. The method of claim 1 wherein said nozzle channel effective diameter $D_2$ is at least 5 percent greater than said chamber wall exit port rim effective diameter $D_1$.

7. The method of claim 1 wherein said inner channel wall nozzle channel effective diameter $D_2$ is at least 10 percent greater than said chamber wall exit port rim effective diameter $D_1$.

8. The method of claim 1 wherein said nozzle channel effective diameter $D_2$ is at least 20 percent greater than said chamber wall exit port rim effective diameter $D_1$.

9. The method of claim 1 wherein said inner channel wall nozzle channel effective diameter $D_2$ is at least 3 percent greater than said chamber wall exit port rim effective diameter $D_1$.

10. The method of claim 1 wherein said inner chamber wall has an inner chamber wall effective diameter $D_3$, and said inner chamber wall effective diameter $D_3$ is greater than said inner channel wall nozzle channel effective diameter $D_2$.

11. A cartridge, adapted to be operated solely by being mounted upon an ejector holder, said cartridge comprising:

an elongated body, said body being molded from rigid plastic material and having a cylindrical body wall, said cylindrical body wall having a cylindrical inner body wall, a predetermined length, uniform interior diameter, a uniform exterior diameter and a central axis, one end of said cylindrical body wall being open and formed at the extremity thereof with an annular relatively short circular exterior flange, said flange being adapted to be detachably mounted within a complementary seat in an ejector type holder, the opposite end of said body being closed by an end wall having a hemispherical exterior surface and an arcing interior surface, said end wall having substantially greater thickness than said cylindrical body wall, a nozzle molded integrally with and extending from said end wall at an obtuse angle to said central axis of said cylindrical body wall to direct discharge from said cartridge to the interior of an oral cavity, said nozzle having a cylindrical nozzle channel with a substantially uniform diameter, an effectively cylindrical inner nozzle wall enclosing said nozzle channel, said nozzle having a nozzle entrance passage, through said end wall to the nozzle, and a channel wall exit orifice rim, said cylindrical inner body wall of said elongated body having a chamber wall exit port rim, opening between said inner chamber wall and said inner nozzle wall, said chamber wall exit port rim having a chamber wall exit port rim effective diameter $D_1$, said inner channel wall nozzle channel having an effective diameter $D_2$, said nozzle channel effective diameter $D_2$ effectively being greater than said chamber wall exit port rim effective diameter $D_1$, and a piston having a side wall and semi-circular front facing portion, said side wall being closely complementary to said cylindrical inner body wall and inserted into the open end thereof and said front facing portion having a complementary shape to said interior surface of said end wall of said elongated body.

12. The cartridge of claim 11 further comprising a cap, said cap being supported by said nozzle.

13. The cartridge of claim 12 wherein said nozzle extends from said body and said cap closes an outer end of said nozzle to seal the contents of the cartridge against ingress of any surrounding contaminating matter.

14. The cartridge of claim 12 wherein said cap is color-coded to indicate desired properties of the contents of the cartridge.

15. The cartridge of claim 11 further characterized by said body and piston being formed from plastic material suitably colored to render the same impervious to the transmission of ambient light, thereby rendering the cartridge adapted to contain light-curable material in a manner to prevent premature curing of such material while stored in such cartridge.

16. The cartridge of claim 11 wherein said wall nozzle channel effective diameter $D_2$ is at least 5 percent greater than said chamber wall exit port rim effective diameter $D_1$.

17. The cartridge of claim 11 wherein said nozzle channel effective diameter $D_2$ is at least 10 percent greater than said chamber wall exit port rim effective diameter $D_1$.

18. The cartridge of claim 11 wherein said nozzle channel effective diameter $D_2$ is at least 20 percent greater than said chamber wall exit port rim effective diameter $D_1$.

19. The cartridge of claim 11 wherein said nozzle entrance passage has a length and said length of said nozzle entrance passage is less than 20 percent of the diameter of said entrance port.

20. The cartridge of claim 11 wherein said nozzle entrance passage has a length and said length of said nozzle entrance passage is more than 3 percent of the diameter of said entrance port.

21. The cartridge of claim 11 wherein said inner chamber wall has an inner chamber wall effective diameter $D_3$, and said inner chamber wall effective diameter $D_3$ is greater than said nozzle channel effective diameter $D_2$.

22. The cartridge of claim 11 wherein said nozzle has a bead circumscribing said nozzle.

* * * * *